(12) United States Patent
White et al.

(10) Patent No.: US 7,799,769 B2
(45) Date of Patent: Sep. 21, 2010

(54) TRANSDERMAL COMPOSITIONS AND METHODS FOR TREATMENT OF FIBROMYALGIA AND CHRONIC FATIGUE SYNDROME

(75) Inventors: Hillary D. White, S. Pomfret, VT (US); Robert Gyurik, Exeter, NH (US)

(73) Assignee: White Mountain Pharma, Inc., New York, NY (US)

( * ) Notice: Subject to any disclaimer, the term of this patent is extended or adjusted under 35 U.S.C. 154(b) by 1274 days.

(21) Appl. No.: 11/303,813

(22) Filed: Dec. 16, 2005

(65) Prior Publication Data
US 2006/0100186 A1 May 11, 2006

Related U.S. Application Data

(63) Continuation of application No. 10/464,310, filed on Jun. 18, 2003, now abandoned.

(51) Int. Cl.
A61K 31/56 (2006.01)
A61K 9/70 (2006.01)
A61K 9/14 (2006.01)
A61F 13/00 (2006.01)
A61L 15/16 (2006.01)

(52) U.S. Cl. .................. 514/170; 514/180; 424/443; 424/444; 424/484

(58) Field of Classification Search .............. 514/170, 514/180
See application file for complete search history.

(56) References Cited

U.S. PATENT DOCUMENTS

| 4,542,129 | A | 9/1985 | Orentreich |
| 5,019,395 | A | 5/1991 | Mahjour et al. |
| 5,206,008 | A | 4/1993 | Loria |
| 5,461,042 | A | 10/1995 | Loria |
| 5,656,606 | A | 8/1997 | Nargund |
| 5,676,968 | A | 10/1997 | Lipp |
| 5,709,878 | A | 1/1998 | Rosenbaum et al. |
| 5,855,905 | A | 1/1999 | Oettel et al. |
| 5,855,920 | A | 1/1999 | Chein |
| 5,869,090 | A | 2/1999 | Rosenbaum |
| 5,935,949 | A | 8/1999 | White ................ 514/178 |
| 5,968,919 | A | 10/1999 | Samour |
| 6,132,760 | A | 10/2000 | Hedenstrom |
| 6,238,284 | B1 | 5/2001 | Dittgen et al. |
| 6,299,900 | B1 | 10/2001 | Reed |

(Continued)

FOREIGN PATENT DOCUMENTS

WO      WO98/36764 A       8/1998

(Continued)

OTHER PUBLICATIONS

Dictionary Definition of "Stabilizer" Academic Press Dictionary of Science and Technology from Elsevier Science and Technology 1992, 1996 by Academic Press.

(Continued)

*Primary Examiner*—San-ming Hui
(74) *Attorney, Agent, or Firm*—Loeb & Loeb, LLP

(57) ABSTRACT

Compositions and methods for alleviating the symptoms associated with chronic fatigue syndrome and fibromyalgia syndrome are provided. The compositions are based on use of a transdermal gel formulation delivery system for androgens, either alone or in combination with other hormones.

14 Claims, 4 Drawing Sheets

U.S. PATENT DOCUMENTS

| | | | |
|---|---|---|---|
| 6,319,913 | B1 | 11/2001 | Mak et al. |
| 6,503,894 | B1 | 1/2003 | Dudley |
| 6,743,448 | B2 | 6/2004 | Kryger |
| 6,818,226 | B2 | 11/2004 | Reed et al. |
| 6,923,983 | B2 | 8/2005 | Morgan et al. |
| 7,169,107 | B2 | 1/2007 | Jersey-Willuhn |
| 7,184,820 | B2 | 2/2007 | Jersey-Willuhn |
| 7,198,801 | B2 | 4/2007 | Carrara |
| 7,214,381 | B2 | 5/2007 | Carrara |
| 7,320,968 | B2 | 1/2008 | Gyurik |
| 7,335,379 | B2 | 2/2008 | Carrara |
| 7,404,965 | B2 | 7/2008 | Carrara |
| 7,470,433 | B2 | 12/2008 | Carrara |
| 7,608,605 | B2 | 10/2009 | Gyurik |
| 7,608,606 | B2 | 10/2009 | Gyurik |
| 7,608,607 | B2 | 10/2009 | Gyurik |
| 7,608,608 | B2 | 10/2009 | Gyurik |
| 7,608,609 | B2 | 10/2009 | Gyurik |
| 7,608,610 | B2 | 10/2009 | Gyurik |
| 2002/0058650 | A1 | 5/2002 | Mak et al. |
| 2002/0150625 | A1 | 10/2002 | Kryger |
| 2002/0183296 | A1 | 12/2002 | Dudley et al. |
| 2003/0022877 | A1 | 1/2003 | Dudley |
| 2003/0027804 | A1 | 2/2003 | van der Hoop |
| 2003/0050292 | A1 | 3/2003 | Dudley et al. |
| 2003/0139384 | A1 | 7/2003 | Dudley |
| 2003/0175329 | A1 | 9/2003 | Azarnoff et al. |
| 2003/0199426 | A1 | 10/2003 | Carrara et al. |
| 2003/0232072 | A1 | 12/2003 | Dudley |
| 2004/0002482 | A1 | 1/2004 | Dudley et al. |
| 2004/0028725 | A1 | 2/2004 | Morgan et al. |
| 2004/0092494 | A9 | 5/2004 | Dudley |
| 2004/0198706 | A1 | 10/2004 | Carrara et al. |
| 2004/0219197 | A1 | 11/2004 | Carrara et al. |
| 2004/0220154 | A1 | 11/2004 | Kryger |
| 2004/0220160 | A1 | 11/2004 | Kryger |
| 2004/0223984 | A1 | 11/2004 | Kryger |
| 2004/0259784 | A1 | 12/2004 | White |
| 2004/0259852 | A1 | 12/2004 | White et al. |
| 2005/0020552 | A1 | 1/2005 | Aschkenasy et al. |
| 2005/0025833 | A1 | 2/2005 | Aschkenasy et al. |
| 2005/0042268 | A1 | 2/2005 | Aschkenasy et al. |
| 2005/0049233 | A1 | 3/2005 | Dudley |
| 2005/0054623 | A1 | 3/2005 | Dudley |
| 2005/0112181 | A1 | 5/2005 | Dudley et al. |
| 2005/0113353 | A1 | 5/2005 | Dudley et al. |
| 2005/0118242 | A1 | 6/2005 | Dudley et al. |
| 2005/0142173 | A1 | 6/2005 | Dudley |
| 2005/0152956 | A1 | 7/2005 | Dudley |
| 2005/0192260 | A1 | 9/2005 | Gyurik |
| 2007/0066532 | A1 | 3/2007 | White |
| 2007/0098775 | A1 | 5/2007 | Carrara |
| 2007/0154533 | A1 | 7/2007 | Dudley |
| 2008/0103120 | A1 | 5/2008 | Gyurik |
| 2008/0108590 | A1 | 5/2008 | Gyurik |
| 2008/0275012 | A1 | 11/2008 | Gyurik |
| 2008/0275013 | A1 | 11/2008 | Gyurik |
| 2009/0118250 | A1 | 5/2009 | Gyurik |
| 2009/0118251 | A1 | 5/2009 | Gyurik |
| 2009/0118252 | A1 | 5/2009 | Gyurik |
| 2009/0124589 | A1 | 5/2009 | Gyurik |
| 2009/0124590 | A1 | 5/2009 | Gyurik |
| 2009/0131387 | A1 | 5/2009 | Gyurik |
| 2009/0192131 | A1 | 7/2009 | Gyurik |
| 2009/0192132 | A1 | 7/2009 | Gyurik |

FOREIGN PATENT DOCUMENTS

| | | |
|---|---|---|
| WO | WO 99/24041 | 5/1999 |
| WO | WO 01/39754 | 6/2001 |
| WO | WO 01/85695 A1 | 11/2001 |
| WO | WO 02/17926 | 3/2002 |
| WO | WO 02/17927 | 3/2002 |
| WO | WO 02/089849 | 11/2002 |
| WO | WO 03/002123 | 1/2003 |
| WO | WO 03/028667 | 4/2003 |
| WO | WO 03/028667 A2 | 4/2003 |
| WO | WO 2004/037173 | 5/2004 |
| WO | WO 2004/080413 | 9/2004 |
| WO | WO 2004/091631 | 10/2004 |

OTHER PUBLICATIONS

Aloisi AM, Ceccarelli I, Fiorenzani P 2003 Gonadectomy affects hormonal and behavioral responses to repetitive nociceptive stimulation in male rats. Ann N Y Acad Sci 1007:232-7.

Aloisi AM, Ceccarelli I, Fiorenzani P, De Padova AM, Massafra C 2004 Testosterone affects formalin-induced responses differently in male and female rats. Neurosci Lett 361:262-4.

Bachmann G, Bancroft J, Braunstein G, et al. 2002 Female androgen insufficiency: the Princeton consensus statement on definition, classification, and assessment. Fertil Steril 77:660-5.

Beatty WW, Fessler RG 1977 Gonadectomy and sensitivity to electric shock in the rat. Physiol Behav 19:1-6.

Cathey MA, Wolfe F, Kleinheksel SM, Hawley DJ 1986 Socioeconomic impact of fibrositis. A study of 81 patients with primary fibrositis. American Journal of Medicine. 81:78-84.

FDA 2003 Meeting of the Arthritis Advisory Committee transcript Jun. 23, 2003. Center for Drug Evaluation and Research (www.fda. gov/ohrms/dockets/ac/cder03.html #Arthritis).

Fields HL, Basbaum AI 1994 Central nervous system mechanisms of pain modulation. In: Wall PD, Meliack R (eds) Textbook of Pain. Oxford Churchill Livingstone Press, New York, pp. 243-257.

Gaumond I, Arsenault P, Marchand S 2002 The role of sex hormones on formalin-induced nociceptive responses. Brain Res 958:139-45.

Gaumond I, Arsenault P, Marchand S 2005 Specificity of female and male sex hormones on excitatory and inhibitory phases of formalin-induced nociceptive responses. Brain Res 1052:105-11.

Groopman J 2000 Annals of medicine: Hurting all over. Nov. 13 issue New Yorker, pp. 78-92.

Heald AH, Butterworth A, Kane JW, et al. 2006 Investigation into possible causes of interference in serum testosterone measurement in women. Ann Clin Biochem 43:189-95.

Jaszmann LJB 1976 Epidemiology of the climacteric syndrome. In: Campbell S (ed) The Management of the Menopause and Postmenopausal Years. University Park Press, Baltimore, pp. 11-23.

Kam K, Park Y, Cheon M, Son GH, Kim K, Ryu K 2000 Effects of immobilization stress on estrogen-induced surges of luteinizing hormone and prolactin in ovariectomized rats. Endocrine 12:279-87.

Liu Z, Welin M, Bragee B, Nyberg F 2000 A high-recovery extraction procedure for quantitative analysis of substance P and opioid peptides in human cerebrospinal fluid. Peptides 21:853-60.

McCain GA 1994 Fibromyalgia and myofascial pain syndromes. In: Wall PD, Melzack R (eds) Textbook of Pain, Third edition ed. Churchill Livingstone, New York, pp. 475-493.

McEwen BS 2002 "The End of Stress As We Know It". Joseph Henry Press, Washington, DC; pp. 55-66 & 107-134.

Melzack R 1999 From the gate to the neuromatrix. Pain. Suppl:S121-6.

Mendell LM 1966 Physiological properties of unmyelinated fiber projection to the spinal cord. Experimental Neurology. 16:316-32.

Moore LB, Goodwin B, Jones SA, et al. 2000 St. John's wort induces hepatic drug metabolism through activation of the pregnane X receptor. Proceedings of the National Academy of Sciences of the United States of America. 97:7500-7502.

Nayebi AR, Ahmadiani A 1999 Involvement of the spinal serotonergic system in analgesia produced by castration. Pharmacol Biochem Behav 64:467-71.

O'Malley PG, Bladen E, Tomkins G, Santoro J, Kroenke K, Jackson JL 2000 Treatment of fibromyalgia with antidepressants: a meta-analysis. J Gen Intern Med 15:659-66.

Pardridge WM, Mietus LJ, Frumar AM, Davidson BJ, Judd HL 1980 Effects of human serum on transport of testosterone and estradiol into rat brain. Am J Physiol 239:E103-8.

Pongratz DE, Sievers M 2000 Fibromyalgia-symptom or diagnosis: a definition of the position. Scandinavian Journal of Rheumatology—Supplement. 113:3-7.
Russell IJ 1998 Advances in fibromyalgia: possible role for central neurochemicals. Am J Med Sci 315:377-84.
Russell IJ, Orr MD, Littman B, et al. 1994 Elevated cerebrospinal fluid levels of substance P in patients with the fibromyalgia syndrome. Arthritis & Rheumatism. 37:1593-601.
Sands R, studd J 1995 Exogenous androgens in postmenopausal women. American Journal of Medicine. 98:76S-79S.
Sternberg WF, Mogil JS, Kest B, et al. 1995 Neonatal testosterone exposure influences neurochemistry of non-opioid swim stress-induced analgesia in adult mice. Pain 63:321-6.
Tsuchiya T, Nakayama Y, Sato A 1992 Somatic afferent regulation of plasma luteinizing hormone and testosterone in anesthetized rats. Jpn J Physiol 42:539-47.
Tsuchiya T, Nakayama Y, Sato A 1992 Somatic afferent stimulation-plasma corticosterone, luteinizing hormone (LH), and testosterone responses in aged male rats under anesthetization. Jpn J Physiol 42:793-804.
Vaeroy H, Helle R, Forre O, Kass E, Terenius L 1988 Elevated CSF levels of substance P and high incidence of Raynaud phenomenon in patients with fibromyalgia: new features for diagnosis. Pain. 32:21-6.
Vaeroy H, Nyberg F, Terenius L 1991 No evidence for endorphin deficiency in fibromyalgia following investigation of cerebrospinal fluid (CSF) dynorphin A and Met-enkephalin-Arg6-Phe7. Pain 46:139-43.
Waxman J, Zatzkis SM 1986 Fibromyalgia and menopause. Examination of the relationship. Postgraduate Medicine. 80:165-167.
Woolf CJ, Thompson SW 1991 The induction and maintenance of central sensitization is dependent on N-methyl-D-aspartic acid receptor activation; implications for the treatment of post-injury pain hypersensitivity states. Pain. 44:293-9.
Yen SS 1999 Chronic anovulation caused by peripheral endocrine disorders. In: Yen SS, Jaffe RB, Barbieri RL (eds) Reproductive Endocrinology. W.B. Saunders Company, Philadelphia, pp. 479-515.
Yunus MB 1992 Towards a model of phatophysiology of fibromyalgia: aberrant central pain mechanisms with peripheral modulation. Journal of Rheumatology, 19:846-50.
Yunus MB, Inanici F 2002 Fibromyalgia syndrome: Clinical features, diagnosis, and biopathophysiologic mechanisms. In: Rachlin ES, Rachlin IS (eds) Myofascial pain and fibromyalgia, Second ediction ed. Mosby Elsevier Science, St. Louis, pp. 3-31.
Balthazart, J. et al., Effects of Clamodulin on Aromatase Activity in the Preoptic Area, Journal of Neuroendocrinology, 2005, vol. 17, 664-671.
Balthazart, J. et al., Interactions Between Kinases and Phosphates in the Rapid Control of Brain Aromatase, Journal of Neuroendocrinology, 2005, vol. 17, 553-559.
Anderberg, Ulla Maria et al., Elevated plasma levels of neuropeptide Y in female fibromyalgia patients, European Journal of Pain (1999) 3: 19-30.
Franke, Werner W., et al., Hormonal doping and androgenization of athletes: a secret program of the German Democratic Republic government, Clinical Chemistry, 43:7, 1262-1279 (1997).
Gracely, Richard H. et al., Functional Magnetic Resonance Imaging Evidence of Augmented Pain Processing in Fibromyalgia, Arthritis & Rheumatism, vol. 46, No. 5, May 2002, pp. 1333-1343.
Wolfe, Frederick, et al., The Prevalence and Characteristics of Fibromyalgia in the General Population, Arthritis & Rheumatism, vol. 38, No. 1, Jan. 1995, pp. 19-28, 1995.
WO 2005/034858 Search Report, Apr. 21, 2005, Hilary D. White.
WO 2005/000236 Search Report, Jan. 6, 2005, Hillary D. White.
Office Action of U.S. Appl. No. 10/464,310 dated May 23, 2005.
Office Action of U.S. Appl. No. 10/464,310 dated Nov. 7, 2005.
Office Action of U.S. Appl. No. 11/555,882 dated Apr. 3, 2009.
Office Action of U.S. Appl. No. 10/677,673 dated May 9, 2006.
Office Action of U.S. Appl. No. 10/677,673 dated Oct. 3, 2006.
Office Action of U.S. Appl. No. 10/677,673 dated Nov. 3, 2005.
Tamburic, Slobodanka et al., An investigation into the rheological, dielectric and mucoadhesive properties of poly (acrylic acid) gel systems, Journal of Controlled Release 37 (1995) 59-68.

Leichtnam Marie-Laure et al., Identification of penetration enhancers for testosterone transdermal delivery from spray formulations, Journal of Controlled Release 113 (2006) 57-62.
Testim 1% (testosterone gel) Prescribing Information.
U.S. Appl. No. 78/146,691 TESS Search Results CPE-215 Filed Jul. 23, 2002.
U.S. Appl. No. 76/006,648 TESS Search Results CPE-215 File Mar. 22, 2000.
Bentley Pharmaceuticals Announces License Agreement for its Topical Testosterone Gel Formulation; License is First for CPE-215 Permeation Technology Dec. 18, 2000.
Bentley Pharmaceuticals Announces Research and Licensing Agreements for Its Topical Testosterone Gel Formulation, Business Wire Jun. 6, 2000.
Osborne, David W. et al., Skin Penetration Enhancers Cited in the Technical Literature, Pharmaceutical Technology 21(11) (1997) 58-66 (5 pages).
Moser, Katrin et al., Passive skin penetration enhancement and its quantification in vitro, European Journal of Phamaceutics and Biopharmaceutics 52 (2001) 103-112.
Karande, Pankaj et al., High Throughput Screening of Transdermal Formulations, Phamaceutical Research, vol. 19, No. 5, May 2002 655-660.
AndroGel (testosterone gel) 1%, Full Prescribing Information, 500122/500127 Rev. Dec. 2007.
Cutter, Christopher B., Compounded Percutaneous Testosterone Gel: Use and Effects in Hypogonadal Men, JABFP, vol. 14, No. 1, Jan.-Feb. 2001, p. 22-32.
Wang, Christina et al., Transdermal Testosterone Gel Improves Sexual Function, Mood, Muscle Strength, and Body Composition Parameters in Hypogonadal Men, The Journal of Clinical Endocronology & Metabolism, vol. 85, No. 8, 2000 2389-2853.
Wang, Christina et al., Pharmacokinetics of Transdermal Testosterone Gel in Hypogonadal Men: Application of Gel at One Site v. Four Sites: A General Clinical Research Center Study, J. of Clin. Endocrinol. & Metab/, vol. 85, No. 3, 2000 964-969.
Bentley Pharmaceuticals Form S-3 Registration Statement Under the Securities Act of 1933, Bentley Pharmaceuticals, Inc., Feb. 15, 2002 pp. 31-36.
Coderre, Terence J. et al., Contribution of central neuroplasticity to pathological pain: review of clinical and experimental evidence, Pain, 52 (1993) pp. 259-285.
Abe-Dohmae et al., Sumiko et al., Neurotransmitter-Mediated Regulation of Brain Aromatase: Protein Kinase C- and G-Dependent Induction, Journal of Neurochemistry, vol. 67, No. 5, 1996, pp. 2087-2095.
McEwen, Bruce S., Neural Gonadal Steroid Actions, Science, vol. 211, Mar. 20, 1981, pp. 1303-1311.
MacLusky, Neil J. et al., Sexual Differentiation of the Central Nervous System, Science, vol. 211, Mar. 20, 1981, pp. 1294-1303.
Fillingim, R.B. et al., Sex-related hormonal influences on pain and analgesic responses, Neuroscience and Biobehavioral Reviews 24 (2000) pp. 485-501.
Costigan, Michael et al., Pain: Molecular Mechanisms, The Journal of Pain, vol. 1, No. 3 (Fall), Suppl 1, 2000, pp. 35-44.
Opstad, Per Kristian, Androgenic Hormones during Prolonged Physical Stress, Sleep, and Energy Deficiency, Journal of Clinical Endocrinology and Metabolism, vol. 74, No. 5, 1992, pp. 1176-1183.
Amini, Hossein, et al., Increase in testosterone metabolilsm in the rat central nervous system by formalin-induced tonic pain, Pharmacology, Biochemistry and Behavior 74 (2002), pp. 199-204.
Anonymous, "Testosterone-Topical Fortigel-Cellegy", Biodrugs 2003 17(4):299-300.
Alberti et al., "Pharmaceutical development and clinical effectiveness of a novel gel technology for transdermal drug delivery", Expert Opin. Drug Deliv 2005 2(5):935-950.
Nathorst-Boos, et al., "Percutaneous administration of testosterone gel in postmenopausal women—a pharmacological study", Gyneclogical Endocrinology 2005 20(5):243-248.
Davis et al., Effects of aromatase inhibition on sexual function and well-being in postmenopausal women treated with testosterone:a randomized, placebo-controlled trial, Menopause:The Journal of the North American Menopause Society 2006 13(1):37-45.

Goldstat et al., "Transdermal testosterone therapy improves well-being, mood, and sexual function in premenopausal women", Menopause:The Journal of the North American Menopause Society 2003 10(5):390-398.

Gruber et al., "Effect of percutaneous androgen replacement therapy on body composition and body weight in postmenopausal women", Maturitas 1998 29:253-259.

Massin et al., "Effects of transdermal testosterone application on the ovarian response to FSH in poor responders undergoing assisted reproduction technique—a prospective, randomized, double-blind study", Human Reproduction 2006 21(5):1204-1211.

Mazer et al., "Transdermal Testosterone for Women:A New Physiological Approach for Androgen Therapy", Obstetrical and Gynecological Survey 2003 58(7):489-500.

Mylonakis et al., "Diagnosis and Treatment of Androgen Deficiency in Human Immunodeficiency Virus-Infected Men and Women", Clinical Infectious Diseases 2001 33:857-864.

Shifren, Jan L., M.D., "The Role of Androgens in Female Sexual Dysfunction", Mayo Clin Proc 2004 79(suppl):S19-S24.

Singh et al., "Pharmacokinetics of a Testosterone Gel in Healthy Postmenopausal Women", The Journal of Clinical Endocrinology & Metanolsim 2006 91:136-144.

Slater et al., "Pharmacokinetics of testerosterone after percutaneous gel or buccal administration", Fertility and Sterility 2001 76(1):32-37.

Amini and Ahmadiani, "Increase in testosterone metabolism in the rat central nervous system by formalin-induced tonic pain", Pharmacol. Biochem. Behav. 2002 74:199-204.

Amandusson et al., Estrogen receptor-like immunoreactivity in the medullary and spinal dorsal horn.

Amandusson et al., "Colocalization of Oestrogen Receptor Immunoreactivity and Preproenkephalin mRNA Expression to Neurons in the Superficial Laminae of the Spinal and Medullary Dorsal Horn of Rats", Eur. J. Neurosci. 1996.

Amandusson et al., Estrogen-induced alterations of spinal cord enkephalin gene expression, Pain 1999.

Bammann et al., "Total and free testosterone during pregnancy", Am. J. Obstet. Gynecol. 1980 137:293-298.

Blomqvist A., "Sex Hormones and Pain:A New Role for Brain Aromatase?", Compar. Neurol. 2000 423:549-551.

Burckhardt et al., "The Fibromyalgia Impact Questionnaire:Development and Validation", J. Rheumatol.

Crofford et al., "Fibromyalgia:Where Are We a Decade After the American College of Rheumatology Classification Criteria Were Developed", Arthr. Rheumat. 2002 46(5):1136-1138.

Dessein et al., "Hyposecretion of adrenal androgens and the relation of serum adrenal steroids, serotonin and insulin-like growth factor-1 to clinical features in women with fibromyalgia", Pain 1999 83:313-319.

Evard et al. "Localization and Controls of Aromatase in the Quail Spinal Cord", J. Compar. Neurol. 2000.

Fletcher et al., "Failure of Estrogen Plus Progestin Therapy for Prevention", J. Amer. Med. Assoc. 2002.

Gintzler A.R., "Endorphin-Mediated Increases in Pain Threshold during Pregnancy", Science 1980 210(Issue.

Goldenberg et al., "A Randomized, Double-Blind Crossover Trial of Fluoxetine and Amitriptyline in the Treatment of Fibromyalgia", Arthrit. Rheumat. 1996 39(11):1852-1859.

Javanbakht et al., "Pharmacokinetics of a Novel Testosterone Matrix Transdermal System in Healthy, Premenopausal Women and Women Infected with the Human Immunodeficiency Virus", J. Clin. Endocrinol. Metab. 2000.

Ma et al., "Substance P and Enkephalin Immunoreactivities in Axonal Boutons Presynaptic to Physiologically Identified Dorsal Horn Neurons. An Ultrastructural Multiple-Labelling Study in the Cat", Neuroscience 1997.

Miller et al., "Transdermal Testosterone Administration in Women with Acquired Immunodeficiency Syndrome Wasting: A Pilot Study", J. Clin. Endocrinol. Metab. 1998 83(8):2717-.

Okun et al., Beneficial Effects of Testosterone Replacement for the Nonmotor Symptoms of Parkinson.

Paiva et al., "Impaired Growth Hormone Secretion in Fibromyalgia Patients", Arthr. Rheumat. 2002.

Tapanainem et.al, "Effect of growth hormone administration on human ovarian function and steroidogenic gene expression in granulosa-luteal cells", Fertility and Sterility 58(4):726-732.

Wolfe, F. et al., "The American College of Rheumatology 1990 Criteria for the Classification of Fibromyalgia".

Baldelli et al., "Growth Hormone Secretagogues as Diagnostic Tools in Disease States", Endocrine 2001 14(1):95-99.

Multon et al., Lack of estrogen increases pain in the trigeminal formalin model: a behavioural and immunocytochemical study of transgenic ArKO mice, Pain 114: 257-265 (2005).

Warner et al., Dehydroepiandrosterone sulphate interferes with the Abbott Architect direct immunoassay for testosterone, Ann. Clin Biochem. 43: 196-199 (2006).

Mease et al., Fibromyalgia Syndrome, J. Rheumatol. 32(11): 2270-2277 (2005).

Richman et al., Low-dose estrogen therapy for prevention of osteoporosis: working our way back to monotherapy, Menopause 13(1): 148-155 (2006).

Melzack et al., Pain Mechanism: A New Theory, Science 150(3699): 971-979 (1965).

Search Report from European Patent Application No. 08154166.6-1216 (Aug. 31, 2009).

TRANSDERMAL COMPOSITIONS AND METHODS FOR TREATMENT OF FIBROMYALGIA AND CHRONIC FATIGUE SYNDROME

This application is a continuation of U.S. Ser. No. 10/464,310 filed Jun. 18, 2003 now abandoned, whose contents are incorporated herein by reference in their entirety.

BACKGROUND OF THE INVENTION

The Women's Health Initiative (WHI) clinical trial, whose aim was to prospectively evaluate the risks and benefits of orally administered combination hormone replacement therapy in healthy women using estrogens and medroxyprogesterone acetate, was recently halted (Fletcher, S. W. et al. 2002. *J. Amer. Med. Assoc.* 288:366-368). The increased risks in coronary heart disease, breast cancer, stroke, and pulmonary embolism outweighed the increased benefits in colorectal cancer, endometrial cancer, hip fractures and death due to other causes, resulting in a small but statistically significant increased risk for the global index of hazard ratios among women taking these hormones. The authors pointed out, however, that their study only evaluated healthy women, not those with symptoms of hormone deficiency. Furthermore, other routes of delivery, e.g. transdermal systems, need to be studied, since it is possible that transdermal delivery may increase benefits and/or decrease risks to these patients. It was noted by the authors of the WHI study that hormone replacement therapy is still considered to be effective for relieving perimenopausal symptoms such as hot flashes.

Most clinical trials evaluating sex hormone replacement therapy have focused on estrogens and progestins, although testosterone replacement therapy in women who may be testosterone deficient is now beginning to be addressed using transdermal delivery systems, e.g. for disease states in which there is stress from chronic disease with loss of muscle mass and chronic fatigue, such as wasting syndrome in women with AIDS (Miller, K. Et al. 1998. *J. Clin. Endocrinol. Metab.* 83:2717-2725; Javanbakht, M. Et al. 2000. *J. Clin. Endocrinol. Metab.* 85:2395-2401). Testosterone replacement therapy using transdermal delivery has also been of benefit to men with symptoms of testosterone deficiency, for example in men with Parkinson's disease (Okun, M. S. et al. 2002. *Arch. Neurol.* 59:1750-1753). There is accumulating evidence that the sex hormones, in particular estrogens, progestins and now testosterone, are important for subjective feelings of well-being and quality of life, parameters that were not assessed in the Women's Health Initiative trial.

U.S. Pat. No. 5,935,949 discloses a method of alleviating the symptoms of fibromyalgia syndrome and chronic fatigue syndrome which involves oral administration of androgens, such as testosterone, to patients. The idea behind the use of testosterone therapy in the treatment of such conditions is that muscle pain and chronic fatigue, primary symptoms in women with fibromyalgia syndrome (FMS), relates, at least in part, to testosterone deficiency, since androgens are known to allow for increased musculature and improvement in fatigue. Indeed, a small decrease in serum free testosterone concentrations has been documented for premenopausal fibromyalgia patients relative to healthy volunteers, but significance was not achieved for postmenopausal women (Dessein, P. H. et al. 1999. *Pain* 83:313-319). A relationship between testosterone and pain sensation has been previously suggested (Blomqvist, A. 2000. *Compar. Neurol.* 423:549-551). Accumulating evidence supports the concept that sex hormones can elevate the pain threshold in an individual, for example, during pregnancy (Gintzler, A. R. 1980. *Science* 210:193-195), when testosterone concentrations, as well as estrogen and progesterone concentrations, are elevated (Bammann, B. L. et al. 1980. *Am. J. Obstet. Gynecol.* 137:293-298). The theory that testosterone can suppress pain is supported by the discovery of aromatase-positive cells in the spinal cord dorsal horn of higher vertebrates (quail), where initial processing of pain sensation occurs (Evard, H. Et al. 2000. *J. Compar. Neurol.* 423:552-564). The presence of aromatase, which converts testosterone to 17β-estradiol, is interesting because it is known that estrogen can induce the transcription of opiates in estrogen receptor-positive cells derived from the superficial layers of the spinal dorsal horn (Amandusson, A. et al. 1996. *Neurosci. Lett.* 196:25-28; Amandusson, A. et al. 1996. *Eur. J. Neurosci.* 8:2440-2445; Amandusson, A. et al. 1999. *Pain* 83:243-248), a location that is important for the synthesis of endogenous opiates. Administration of estrogen to ovariectomized female rats has been demonstrated to increase spinal cord enkephalin transcription (Amandusson, A. et al. 1999. *Pain* 83:243-248), and estrogen receptor-positive cells co-localize with preproenkephalin mRNA (Amandusson, A. et al. 1996. *Eur. J. Neurosci.* 8:2440-2445). These endogenous opiates act on enkephalinergic neurons to mediate inhibition of nociceptive relay cells, both in primary afferent fibers as well as in pain-modulating fibers descending from the brainstem (Ma, W. Et al. 1997. *Neuroscience* 77:793-811). Thus, both testosterone and estrogen appear to be important for modulating the sensation of pain. However, the differential importance of androgens versus estrogens in pain sensation relative to gender remains poorly understood.

Testosterone may also act at the level of the brain. Testosterone concentrations were dramatically decreased in the brain and spinal cord of rats in response to pain-inducing subcutaneous injections of formalin into the paw. In these animals, the loss of testosterone in the central nervous system was demonstrated to be due to its metabolism by 5α-reductase to dihydrotestosterone (Amini, H. Et al. 2002. *Pharmacol. Biochem. Behav.* 74:199-204). These authors pointed out that dihydrotestosterone can be metabolized to 5α-androstane-3α,17β-diol, which is an effective modulator of $GABA_A$ receptor complexes in the brain. $GABA_A$ receptors are found throughout the brain, and actions of $GABA_A$ receptor modulators in the limbic system, specifically in the amygdala, are associated with feelings of fear. The $GABA_A$ receptor ion channel complex is one of the most important inhibitory ion channels in the brain. Thus, testosterone may be important not only for modulation of pain but also for feelings of emotional well-being via binding of its metabolites to the neurosteroid site of the $GABA_A$ receptor, although this remains to be demonstrated.

Other hormones such as growth hormone may also play a role in the pathogenesis and symptoms of fibromyalgia and chronic fatigue. For example, studies have shown that fibromyalgia patients fail to exhibit a proper growth hormone response to acute exercise, a response that is likely related to increased levels of somatostatin a powerful inhibitor of growth hormone synthesis (Crofford, L. J. et al. 2002. *Arthr. Rheumat.* 46:1136-1138; Paiva, E. S. et al. 2002. *Arthr. Rheumat.* 46:1344-1350). It is well known that testosterone increases growth hormone secretion. Growth hormone secretion is reduced in senescence beyond the reduced levels of secretion seen in adult life after puberty. This reduction is thought to relate to the decreased lean body mass to adipose mass ratio known to occur in some individuals in senescence. Thus, increased somatostatin levels may reflect decreased anabolism and decreased muscle mass due to decreased testosterone and growth hormone concentrations in fibromyalgia patients. As a result, therapy with growth hormone may improve the condition of patients with fibromyalgia.

It has now been found that transdermal hormone therapy in women can raise serum hormone concentrations to levels that approximate those normally found in premenopausal women, as well as relieve symptoms in patients with fibromyalgia.

SUMMARY OF THE INVENTION

An object of the present invention is a composition for increasing androgen levels in blood which comprises an androgen at a concentration of about one percent and a pharmaceutically acceptable gel. The androgen compounds of the instant invention may comprise testosterone and its derivatives.

Another object of the present invention is administration of the androgen gel formulation along with compounds that increase levels of growth hormone in blood, or growth hormone itself.

Another object of the present invention is a method of alleviating the symptoms of fibromyalgia syndrome and chronic fatigue syndrome which comprises administering to a patient suffering from fibromyalgia syndrome or chronic fatigue syndrome an effective amount of the androgen gel formulation so that the symptoms are alleviated. In other embodiments of this method the administered product can be a gel with a combination of androgen hormones as well as compounds that increase levels of growth hormone in blood. Further, the method of the invention contemplates administration of the androgen gel formulation and separate injection of growth hormone in the patients.

DETAILED DESCRIPTION OF THE INVENTION

Figure 1:
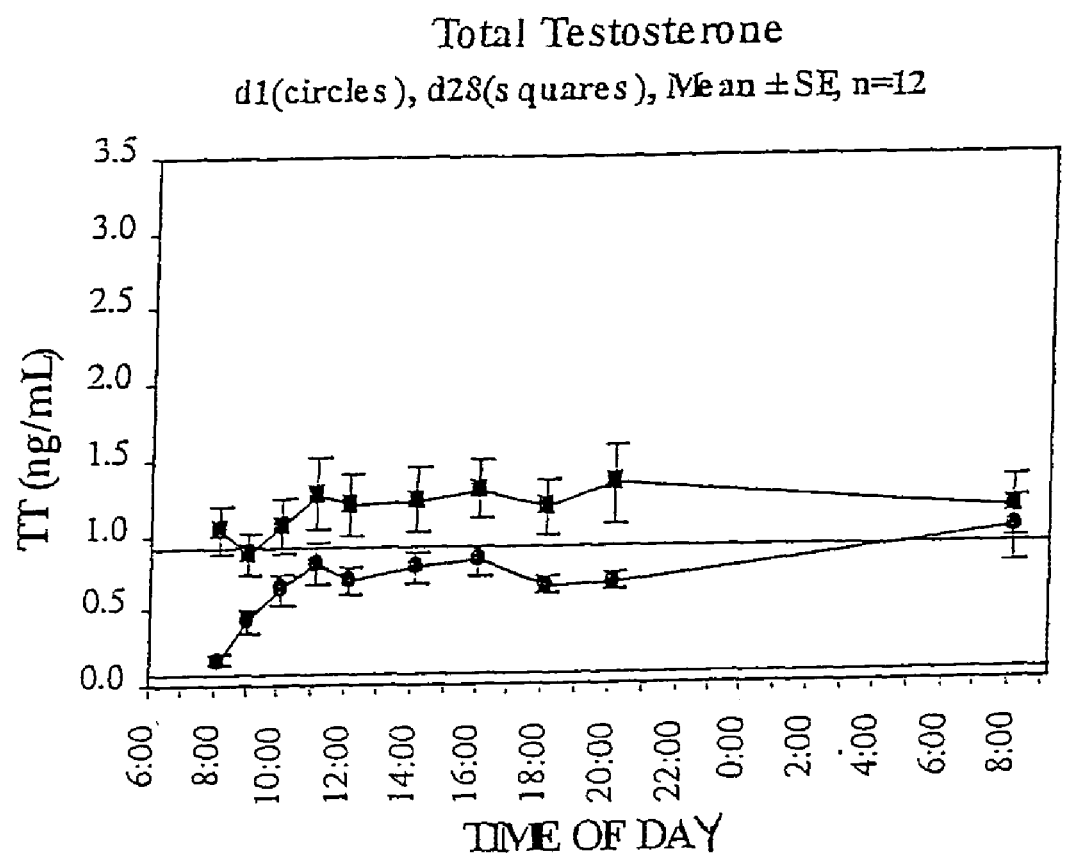
FIG. 1 depicts the levels of total testosterone in blood of the patients, an average of the group, over time on day 1 (shown with circles) and day 28 (shown with squares).

The syndrome of chronic fatigue has received much attention lately. No physical finding or laboratory test can be used to confirm diagnosis of chronic fatigue syndrome. However, this syndrome is generally characterized by fatigue persisting or relapsing for more than six months occurring concurrently with at least four or more of the following symptoms: impaired memory or concentration, sore throat, tender cervical or axillary lymph nodes, muscle pain, multi-joint pain, new headaches, unrefreshing sleep, and post exertion malaise. Early studies suggested an infectious or immune dysregulation mechanism for the pathophysiology of chronic fatigue syndrome. More recent studies have shown that neurologic, affective and cognitive symptoms also frequently occur.

Fibromyalgia (also referred to as fibrositis) is one of the most common rheumatic syndromes in ambulatory general medicine affecting 3-10% of the general population. Most patients with Fibromyalgia Syndrome (FMS) are women, and of these patients, approximately 50-75% are women in their peri-postmenopausal years, aged 40-60. Approximately 2-5% of peri/post menopausal women are affected by FMS, with some estimates ranging from 0.5 to 20%. This disease is characterized by chronic widespread musculoskeletal pain syndrome with multiple tender points, fatigue, headaches, lack of restorative sleep and numbness. Fibromyalgia shares many features with chronic fatigue syndrome including an increased frequency in peri/post menopausal woman, absence of objective findings and absence of diagnostic laboratory tests. Further, these conditions have overlapping clinical features including chronic fatigue, headaches and lack of restorative sleep with musculoskeletal pain predominating in fibromyalgia and apparent increased susceptibility or hyperimmunologic responsiveness to infection predominating in chronic fatigue syndrome.

Various treatments for chronic fatigue syndrome including acyclovir, oral and vaginal nystatin and fluoxetine have been tried with little success. Placebo-controlled trials have demonstrated modest efficacy of amitriptyline, fluoxetine, chlorpromazine, or cyclobenzaprine in treating fibromyalgia. Exercise programs have also been suggested as beneficial in both conditions. Accordingly, there is clearly a need for better treatments for these debilitating conditions.

It has now been found that transdermal administration of hormones, including androgens, can alleviate symptoms in patients suffering from FMS or CFS. By "androgen therapy" it is meant to include administration of a single androgen or a combination of androgens. By "alleviate" it is meant to make less hard to bear, reduce or decrease, or lighten or relieve patients of the symptoms of FMS of CFS. By "symptoms" of FMS or CFS it is meant to include muscle pain and atrophy, chronic fatigue, lack of restorative sleep, increased susceptibility to infection and headaches resulting from FMS or CFS.

A clinical trial was performed to investigate the pharmacokinetics and efficacy of transdermal delivery of hormones for treatment of fibromyalgia. Women were recruited by institutional review board-approved advertising. Subjects aged 40-55 and diagnosed for fibromyalgia using American College of Rheumatology criteria (11/18 bilateral tender points above and below the waist, chronic fatigue, etc., (Wolfe, F. et al. 1990. *Arthrit. Rheumat.* 33:160-172) were selected for the study if they fit additional criteria. Women were included if, in addition to meeting all other criteria, they agreed to keep their medicines unchanged during the study (decreases in analgesics were permitted). Women taking hormone replacement therapy were enrolled if they agreed to come off hormone therapy at least 2 weeks prior to, and for the duration of, the study, in addition to meeting other eligibility criteria. Pre- or peri-menopausal women were required to have adequate alternative contraception, a negative pregnancy test, and treatment was started within the follicular (proliferative) phase of the menstrual cycle. Patients were included if they were willing to exercise 20 minutes a day, 5 days per week during therapy, to promote the effects of testosterone; this was a requirement put in place by the Institutional Review Board.

Children, pregnant women, and women on hormone therapy, hormone contraceptives or infertility drugs were excluded. Women were excluded from the study if they reported undiagnosed vaginal bleeding, had a body mass index BMI >30, admitted to ethanol or illicit drug abuse, had active thrombophlebitis, breast cancer, hypertension (BP>160 systolic/95 diastolic with or without medication, after sitting 5 minutes), or major skin disease, acne or hirsutism. Prior to enrollment, study patient blood was tested for the following general health criteria (exclusion criteria in parentheses): cardiac risk factors by lipid profile—total fasting cholesterol (>240 mg/dL), high density lipoprotein (<35 mg/dL), low density lipoprotein (>210 mg/dL), triglyceride (>300 mg/L); hepatic function by alanine aminotransferase (>1.5×N, normal at 0-40 U/L), alkaline phosphatase (>2×N, normal at 40-120 U/L), aspartate aminotransferase (>1.5×N, normal at 10-30 U/L), serum albumin (>N, normal at 3.2-5.2 g/dL), total bilirubin (>N, normal at 0.2-1.3 mg/dL), and direct (conjugated, soluble) bilirubin (>N, normal at 0.0-0.3 mg/dL); kidney function by blood urea nitrogen (>2×N, normal at 8-18 mg/dL) and serum creatinine (>N, normal at 0.7-1.2 mg/dL) tests; hematological function was assessed by complete blood cell count including testing for hemoglobin (normal, 12-16 g/dL). Blood tests and physical exam at the end of the study were performed to assess whether testosterone therapy adversely affected the general health of the study patient. Serum total testosterone (>0.4 ng/mL) and FSH (<22 IU/L) were tested as well (8AM after overnight fasting), to confirm patients had concentrations of testosterone in the lower half of the reference range (2 patients out of 18 were excluded based on testosterone concentrations) and to determine their postmenopausal status. FSH concentrations <22 IU/L indicated premenopausal or perimenopausal status and thus the need for adequate contraception, unless the patient had undergone bilateral oophorectomy. Testosterone serum concentrations were tested at 8AM due to the small circadian rhythm of circulating androgens. The most frequent exclusion criterion was for BMI >30. Patients were required to stop taking St. John's wort, since St. John's wort is known to induce catabolism of hormones by activating CYP3A, a detoxifying enzyme complex in the liver. Twelve patients who fit the eligibility criteria, above, were scheduled for physical exams including tender point assessment, verification of fibromyalgia diagnosis, and assessment of general health.

On day 1, blood was drawn by venipuncture at 0, 1, 2, 3, 4, 6, 8, 10, 12 and 24 hrs for 24 hr pharmacokinetic profiling of baseline testosterone serum concentrations. Testosterone gel, 0.75 g 1% w/w, was applied by the patient to their lower abdominal skin just after the zero time point blood draw (8AM). The patient also filled out a pain assessment questionnaire form and was given packets of testosterone gel for 8:00 AM daily application to lower abdominal skin, instructions for use and a patient medication log and exercise log for 28 days of therapy. On day 28, the blood draws for 24 hr pharmacokinetic profiling were repeated, and a follow-up exam was repeated at the end of the 28 days of therapy.

The delivery vehicle for this study was a gel formulation. It was chosen for use as a goal of the study was to identify a transdermal delivery system for hormones that would result in effective levels of hormones in blood as a way to reduce side effects of androgen therapy. The gel used for this study was a 1% w/w testosterone gel, USP grade. The daily gel dose applied was 0.75 grams; an expected bioavailability of 10% would deliver 0.75 mg testosterone over 24 hr. The gel was formulated for women by Bentley Pharmaceuticals, Inc. (North Hampton, N.H.) using good manufacturing practice standards, and is colorless, comfortable on the skin, and non-staining.

Testosterone concentrations were determined by enzyme linked immunoassay (EIA, Diagnostic Systems Laboratories or DSL, Inc, Webster, Tex.), where serum testosterone from study subjects competed with enzyme-linked testosterone bound to anti-testosterone mAb. This assay system was designed to detect the lower concentrations of testosterone found in women as well as concentrations in the upper ranges. Free testosterone concentrations were determined by EIA using an anti-testosterone antibody that recognizes the unbound testosterone in the test sample, and has low affinity for sex hormone binding globulin and albumin. For the purposes of determining mean testosterone concentrations, times were based on the nearest hour. Of the 240 time points taken for the pharmacokinetic data (10 time points per individual×2 sets per individual×12 individuals), 1 time point was missed (#012, 4 hr point) and 3 additional time points were in between the standard times for taking blood (#010, 8 hr point; #012, 4 hr and 10 hr points). Values for these time points were derived by interpolation for the purposes of deriving mean testosterone concentrations. A noncompartmental pharmacokinetic analysis using WinNonlin Pro (Pharsight, Mountain View, Calif.) used the exact time points recorded for all the patients.

In order to determine the efficacy of the treatment for reducing symptoms of fibromyalgia, patients filled out questionnaire forms on day 1 and again at the end of therapy on day 28 to assess pain. The patient questionnaire was based on a published and validated Fibromyalgia Impact Questionnaire as well as other accepted criteria for fibromyalgia patient assessment (Wolfe, F. et al. 1990. *Arthrit. Rheumat.* 33:160-172; Goldenberg, D. Et al. 1996. *Arthrit. Rheumat.* 39:1852-1859; Burckhardt, C. S. et al. 1991. *J. Rheumatol.* 18:728-733), and used a 100 mm visual analog scale (VAS). Tender point exams were administered by a qualified rheumatologist experienced in treating women with fibromyalgia, and involved applying approximately 9 pounds of pressure at each tender point and asking whether the patient felt pain. This practice is in accordance with criteria specified by the American College of Rheumatology. Exams were administered just prior to Day 1 of therapy (and therefore designated as "pretreatment"), and at the end of therapy. The pretreatment tender point assessment was performed on all patients within 1 week before the start of therapy. Dolorimeter readings were taken from the bilateral second costochondral junction and trapezius tender points, for comparison, in 11 of the 12 study subjects.

Pharmacokinetic analysis of serum testosterone concentration data was carried out using WinNonlin Pro software, using the noncompartmental model with extravascular input. Differences between Day 1 and Day 28 maximum plasma concentrations ($C_{max}$) and area under the curve (AUC) of a plot of plasma concentrations over time were assessed by calculating individual subject Day 28 minus Day 1 data and estimating 95% confidence intervals of this difference to determine if significance (p<0.05) was reached. Tender point data evaluations were analyzed by Student's t test (paired, 2-tailed).

Analysis of the blood testosterone concentration data revealed that serum total testosterone concentrations were reliably increased in fibromyalgia patients in response to testosterone gel hormone replacement therapy. Serum total testosterone concentrations vs time data for Day 1 and Day 28 are shown in FIG. 1. Comparison of the serum testosterone data to standard reference ranges for the concentration of total testosterone in serum from women confirmed that the fibromyalgia patients in this study initially had total testosterone concentrations in the lower half of the reference ranges. However, the mean serum concentration of total testosterone 24 hr after application of the first dose of hormone on Day 1 was significantly higher than the mean serum concentration for time zero on Day 1 (FIG. 1, p=0.01), indicating that serum concentrations were sustained, on average, early on during the 28 day time course. Steady state concentrations were reached by day 28, as evidenced by the similar mean concentrations at the beginning and end of the 24 hr sampling (see FIG. 1). There was variation in the 24 hr profiles for serum testosterone when analyzed on an inter-individual basis, consistent with the complex regulation known for this hormone. Summary pharmacokinetic parameter analysis demonstrated significantly increased mean total testosterone maximum concentration in response to testosterone therapy: $C_{max}$ was 1.92 ng/mL on day 28 compared with 1.21 ng/mL on day 1, p <0.05. Significantly increased mean total testosterone area under the curve values (assessed over the 24 hr profiling time period) were also found: AUC was 28.75 ng-h/mL on day 28 compared with 18.36 ng-h/mL on day 1, p<0.05. Considered together the pharmacokinetic data demonstrated that with therapy, mean serum total testosterone concentrations initially rose quickly over the first 3 hours and were then reliably sustained over time. In addition, mean serum concentrations were raised from the lower boundary of the reference range to just above the upper end of the reference range for premenopausal women.

Figure 2:
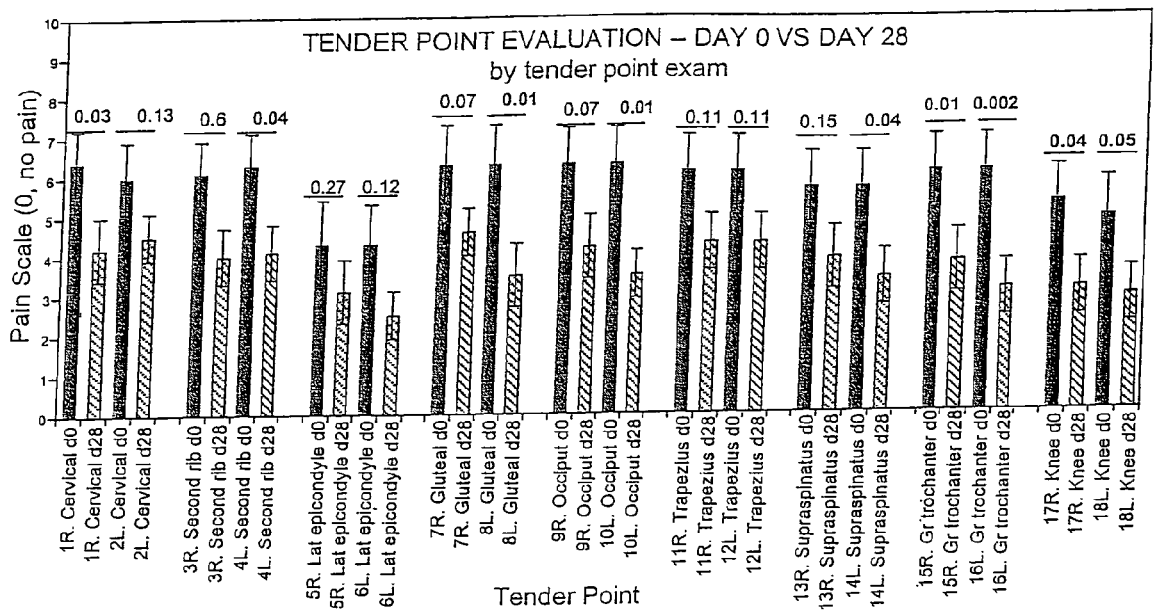
FIG. 2 depicts the results of the tender point evaluations pre-treatment (day 0) and at the end of the study (day 28). The results reported are levels of pain on a scale of 0 (no pain) to 10 (highest level of pain).
Figure 3:
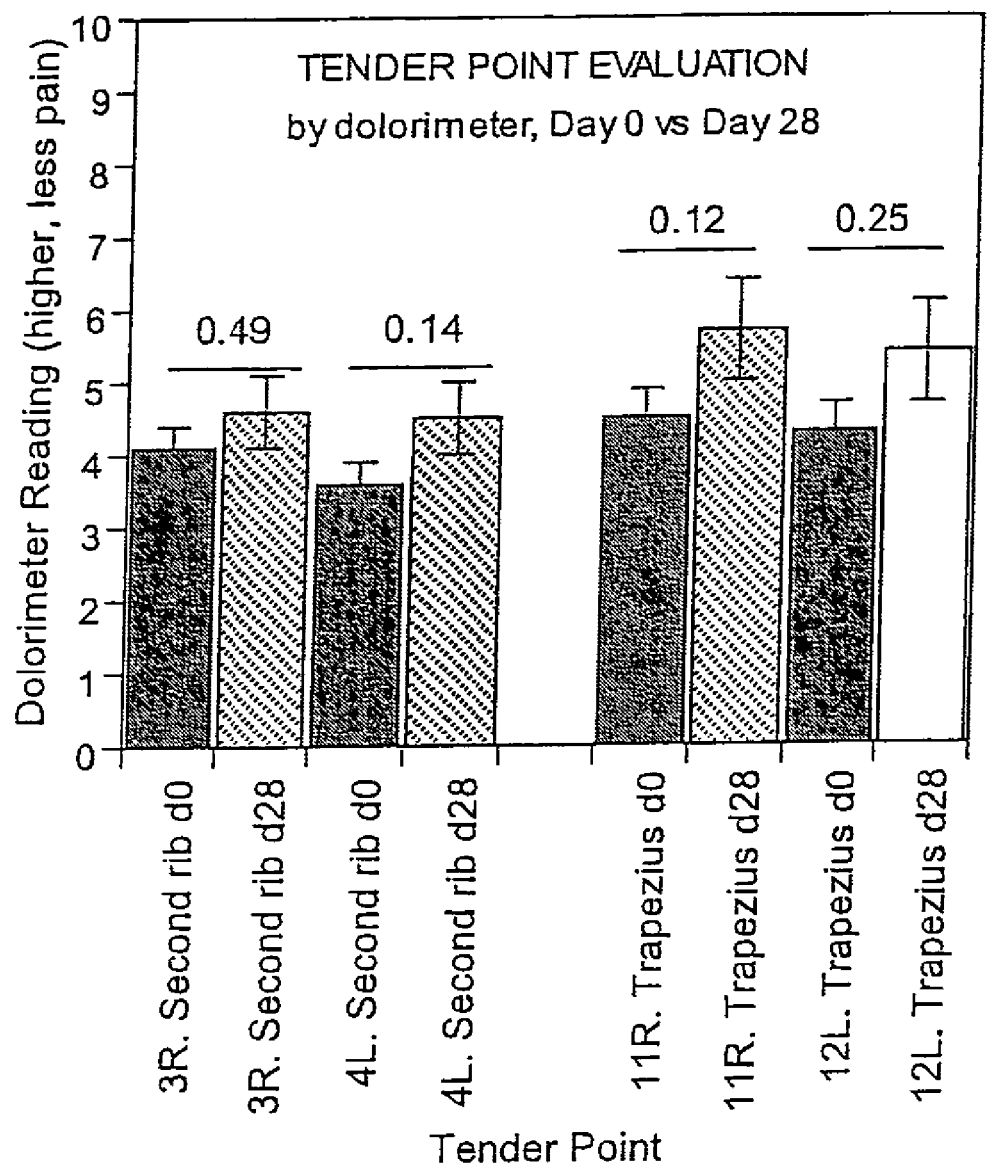
FIG. 3 depicts the results of the dolorimetry assessment of tender point pain pre-treatment (day 0) and at the end of the study (day 28).

Concentrations of free testosterone in serum were also examined and subjected to pharmacokinetic analysis. Results similar to total testosterone results were obtained. However, two of the twelve patients had unusually high concentrations of free testosterone prior to, and throughout, the course of therapy. Individual profiles for the remainder of the patients showed concentrations that increased from the postmenopausal range to the premenopausal and upper postmenopausal reference range. Summary pharmacokinetic parameter analysis showed a mean free testosterone $C_{max}$ of 4.69 pg/mL on day 28 compared with 3.68 pg/mL on day 1 (p>0.05) and a mean free testosterone AUC of 71.38 pg-h/mL on day 28 compared with 54.35 pg-h/mL on day 1 (p>0.05). Free testosterone $C_{max}$ and AUC were increased with therapy, as evidenced by subtraction of the day 1 baseline from day 28 values, but statistical significance was not achieved in these pharmacokinetic parameters due to the two individuals with exceptionally high free testosterone concentrations. The high concentrations of free testosterone in those two patients contrasted with the normal total testosterone profiles for these particular individuals, raising the possibility that these high free hormone concentrations may have resulted from low sex hormone binding globulin concentrations in their serum, although other explanations exist. The only medication or supplement reported by both of these study subjects, and not used by any other subjects, was ginger root. (It is not known if ginger root interferes with the enzyme linked immunoassay for free testosterone, or with sex hormone binding globulin metabolic or binding parameters.) Analysis of the tender point pain data showed that transdermal testosterone gel therapy was associated with decreased subjective assessments of pain. Using a pain scale of 0 to 10, where zero is no pain, there were mean decreases in pain for every tender point, with statistical significance achieved in 9 of 18 categories assessed (categories assessed are listed below in Table 1; results shown in FIG. 2. Using a dolorimeter to assess pain at the same office visit, pain responses were quantitated for the bilateral second costochondral junction and bilateral trapezius tender points (FIG. 3). Individual response values ranged from 2 to 9. Mean dolorimeter values for the pressure at which patients reported pain were higher at the end of 28 days of testosterone treatment, which would be expected if therapy increased thresholds of pain, although the dolorimetry results did not reach statistical significance.

TABLE 1

Tender Points Evaluated

| Tender Point # | Tender Point | Description | Lay Description |
|---|---|---|---|
| 1-2 | lower cervical | bilateral lower cervical (paraspinals) at the anterior aspect of the intertransverse spaces at C5-7 | at the base of the neck in the back |
| 3-4 | second rib | bilateral at the second costochondral junction (rib-cartilage) just lateral to the junction of the upper surface | on the breast bone |
| 5-6 | lateral epicondyle | bilateral lateral epicondyle in forearm, 2 cm distal to the epicondyles | on the outer edge of the forearm about an inch below the elbow |
| 7-8 | gluteal | bilateral gluteal in the upper outer quadrant of buttock in the anterior fold of muscle | on the outside of the hip |
| 9-10 | occiput | bilateral occiput at the insertion of the suboccipital muscle | At the base of the skull beside the spinal column |
| 11-12 | trapezius | bilateral trapezius at midpoint of the upper border | on top of the shoulder toward the back (flat triangular muscle post, neck, shoulder) |
| 13-14 | supraspinatus | bilateral supraspinatus at its origin above the scapular spine near the nedial border | over the shoulder blade |
| 15-16 | greater trochanter | bilateral greater trochanter posterior to the trochanteric prominence | at the top of the hip |
| 17-18 | knee | bilateral knee at the medial fat pad just proximal to the joint line | on the fat pad over the knee |

1-8 anterior, 9-18 posterior

Figure 4:
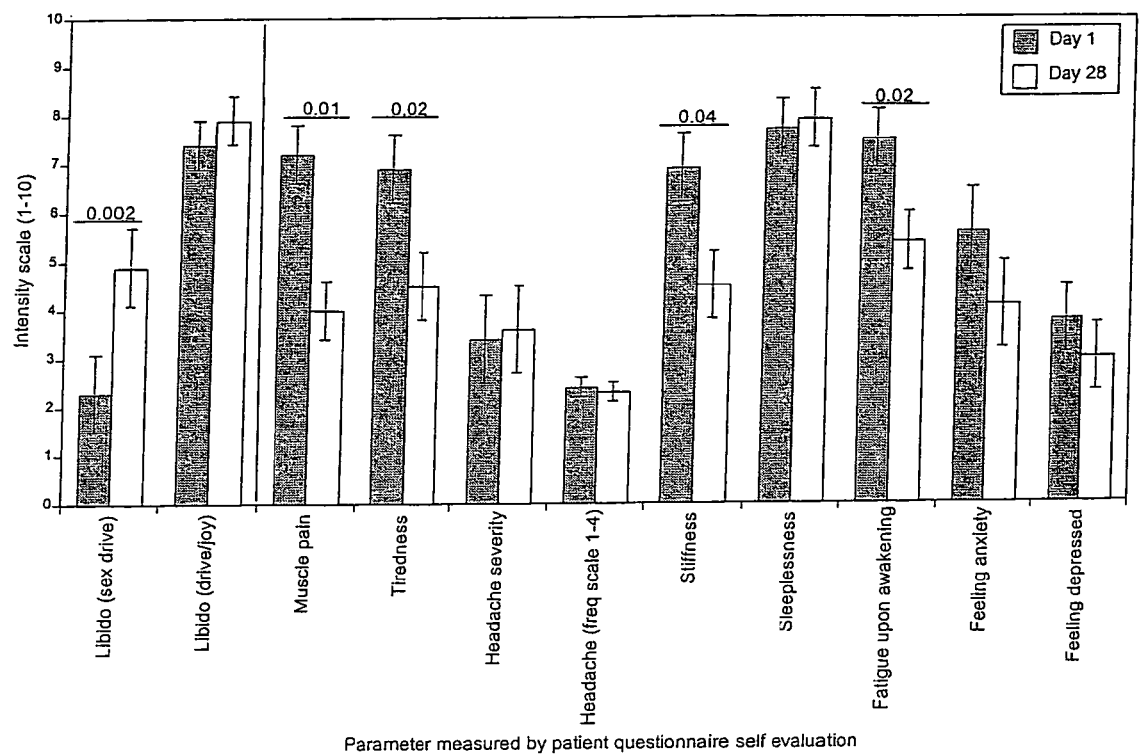
FIG. 4 depicts the severity of symptoms/conditions associated with fibromyalgia and chronic fatigue on a scale of 1 to 10 (10 being the highest increased level) on day 1 versus day 28 of the study. The symptoms/conditions assessed included libido, muscle pain, tiredness, headache severity, headache Frequency, stiffness, sleeplessness, fatigue upon awakening, anxiety, and depression.

Pain parameters were also evaluated by patient questionnaire using a visual analog scale (VAS) from 0-10 (FIG. 4). Libido (sex drive) was increased in response to testosterone treatment. Muscle pain, tenderness, stiffness and fatigue upon awakening were all decreased during testosterone treatment. These findings are consistent with the idea that restoration of premenopausal serum testosterone concentrations relieves symptoms that most specifically relate to testosterone deficiency, e.g. loss of sexual desire, loss of muscle function and increased fatigue. Blood tests and physical exam at the end of the study verified testosterone therapy did not adversely affect the general health of the study patient, and no study patient reported any adverse events that were attributable to the treatment.

Most trials involving hormone replacement therapy have used derivatives of hormones naturally found in women. These derivatized hormones have been promoted because of their patentability and their extended half life. Androgens are no exception since the androgen hormone most prescribed for women is methyltestosterone, where methylation at the C-17 position increases its oral bioavailability. A subset of patients do not tolerate derivatized hormones very well, however.

Non-derivatized exogenous hormones that are structurally identical to endogenous hormones have short plasma/serum half lives that range from 10-100 minutes, making oral administration of native hormones problematic. Investigators have begun to develop transdermal delivery systems, which provide sustained delivery while minimizing hepatotoxicity. A testosterone skin patch has been effective in HIV seropositive women with wasting syndrome (Miller, K. et al. 1998. *J. Clin. Endocrinol. Metab.* 83:2717-2725; Javanbakht, M. et al. 2000. *J. Clin. Endocrinol. Metab.* 85:2395-2401), but the skin patch causes topical skin irritation in many women, making its use problematic.

The present invention involves use of a testosterone formulated as a gel in a concentration that is appropriate for women. The data have shown this formulation to provide effective systemic delivery of testosterone in patients with fibromyalgia. 28 days of therapy with 0.75 g 1% (w/w) testosterone gel per day raised serum concentrations of total and free testosterone in fibromyalgia patients to concentrations approximating those in premenopausal women. At this dose, patients showed significantly decreased muscle pain, decreased stiffness, decreased fatigue and increased libido in response to testosterone therapy. Tender point pain was decreased, as well. These results, from both the pharmacokinetic and pain assessment standpoints, support the use of testosterone replacement therapy to treat individuals with fibromyalgia syndrome.

Accordingly, androgen therapy provides a useful means for alleviating symptoms associated with FMS or CFS in women preferably of peri/post menopausal age. By peri/postmenopausal age it is most often meant to be approximately 40 to 60 years of age. Women outside of this range may also benefit since these syndromes have been known to be present in women 20 to 60 years of age. In a preferred embodiment, the androgen administered comprises testosterone, an active metabolite of testosterone such as dihydrotestosterone or androstenedione or a testosterone derivative such as methyltestosterone, testosterone enanthate or testosterone cypionate. Examples of available pharmacologic preparations of androgens believed to be useful in this invention include, but are not limited to danazol, fluoxymesterone, oxandrolone, methyltestosterone, nandrolone decanoate, nandrolone phenpropionate, oxymethalone, stanozolol, methandrostenolone, testolactone, pregnenolone and dehydroepiandrosterone (DHEA).

In the present invention, the androgens are administered transdermally in a gel formulation. This formulation has advantages over current oral methods as well as transdermal patch methods that include improved bioavailability and a low side effect profile. In a preferred embodiment, a combination of androgens such as testosterone or a testosterone derivative and DHEA can be administered to alleviate both the muscular and neurological symptoms of FMS or CFS.

As will be obvious to those of skill in the art upon this disclosure, other pharmaceutically acceptable androgen therapies can be used. Effective amounts and routes by which the androgen or combination of androgens can be administered in the present invention can be routinely determined by those skilled in the art in accordance with other uses for androgen therapies.

The composition of the present invention comprises, in addition to the aforementioned androgen/anabolic agent, co-treatment with a pharmaceutically effective amount of growth hormone elicitor or effector, either growth hormone or an agent that is known to release growth hormone in effective amounts, i.e., a growth hormone releasing agent ("GRF"). GRF is an acronym based on the existence of an endogenous hormone known as GHRH. Other agents include GHrelin or a growth hormone releasing peptide or analog (GHRP; GHRP-6, or hexarelin, His-DTrp-Ala-Trp-DPhe-Lys, and GHRP-2, or Dala-D-2-NaI-Ala-Trp-Dphe-Lys are examples), which have been shown to release effective amounts of growth hormone. The natural rhythm of growth hormone release from the pituitary gland results in release of insulin-like growth factor (IGF-1), which in general, is considered to be the causal agent that determines the course of hormonal regulation and balance in processes such as adipogenesis and myogenesis. The hormonal effector, then, for the purpose of this invention, is also prophetically considered to be any peptide or peptidomimetic agent that directly acts to release this secondary anabolic growth factor, (IGF-1), not necessarily through the intermediary route of secretion of growth hormone itself. Although the indirect growth hormone route is preferred to elicit IGF-1, the latter route to directly release IGF-1 also is included by example.

In another embodiment of the present invention, the composition comprises a pharmaceutically effective amount of a growth hormone or, more preferably, a growth hormone-releasing agent, or an elicitor of IGF-1 secretion, coupled with androgen treatment and such combined treatment being capable of counteracting the deleterious effects of aging, such as, for example, muscle weakness, body fat increases, and skin fragility in adults. Essentially any suitable growth hormone-releasing agent may be employed in combination with any androgen, preferably one such as testosterone that possesses strong anabolic activity. Other anabolic agents that are not thought of as androgenic agents, or do not possess maximal androgenic activity may be used, as long as they have appreciable anabolic activity. In fact, this invention anticipates, and includes as a prophetic example, those anabolic agents that may be completely devoid of androgenic activity. Examples of such growth hormone-releasing agents include: somatoliberins; growth hormone-releasing hormone active fragments, such as, for example, hGRF (1-29) amide and hexarelin (GHRP-6). Hexarelin is a growth hormone releasing peptide mimetic agent, i.e., it mimics the effects of growth hormone releasing peptide in the body and contains between 2 and 20 amino acids. In particularly preferred embodiments, more than one growth hormone-releasing agent may be used in combination. A preferred combination comprises growth hormone-releasing factor (GRF or GHRH) and a growth hormone releasing peptide or peptidomimetic (GHRP). This combination has been reported to act by separate mechanisms for the release of endogenous growth hormone, and the effects have been shown in some cases to be additive, or even, synergistic, working at a separate receptor often called the Ghrelin receptor, to differentiate it from the GHRH receptor. Since the GHrelin receptor has recently been elucidated, prophetically other ligands for this receptor are anticipated to be synthesized and/or discovered in the future, and these are included by example (Baldelli, R et. al. *Endocrine* 14 (1):95-99, 2001). These are often referred to as GHSs (growth hormone secretagogue).

The administration of a GH or IGF-1 secretagogue will reduce plasma androgen concentration in humans (Tapanainem J et. al, *Fertility and Sterility* 58: 726-732). This effect increases the need for exogenous androgen, such as testosterone, to be also administered as a co-treatment to restore and amplify existing levels.

Other compounds are known to affect this system which is known as the hypothalamo-pituitary-hepatic axis for GH, among other terms. Prophetically, it is probable that other compounds involved in this hormonal regulatory system may play a role in indirectly or directly influencing and increasing levels of GH, IGF-1, or IGF-2, and may be administered in the context of this invention along with the androgenic supplementation to get maximal effects of the growth/anti-aging effects of such treatment. Other indications that may be treated besides fibromyalgia may be syndromes affecting the growth of individuals, including but not limited to pituitary dwarfism, conditions or syndromes that are well known to practitioners in the field of endocrinology, growth, and aging.

For the administration of the GH agents that are described in detail above, they may be administered by a variety of means. These agents may be administered separately from the androgen administration, using the modalities of intranasal, transdermal, parenteral (subcutaneous or intravenous), or oral (with or without permeation enhancement and preferably with enteric protection, since proteins and peptides may be degraded by gastric exposure). GH itself is most preferably administered by parenteral means in practice, because it is a large protein that is of limited stability and limited absorption. However, intranasal administration is also an acceptable means for this and other large proteins or peptides. After the administration modality is chosen for the GH agent, the androgen may be administered in a separate treatment with a different regimen. The desired method for androgen administration is preferably oral, transdermal, intravaginal, or intranasal delivery, although it is most preferred to be administered transdermally in the form of a gel or patch. The literature is replete with examples of compositions suitable in the context of this disclosure for the transdermal administration of these compounds in solution, gel, emulsion, or patch forms.

In addition to a separate delivery modality for the GH agent and the androgenic compound selected for treatment, the two may be combined in a single combination therapy. For example, both could be incorporated together in an oral form, tablet, or suspension, with the caveat that any proteinaceous agent is suitably protected from gastric degradation. Alternatively, the combination of agents may be administered intranasally in one unit through separate delivery chambers, known to those of skill in intranasal delivery, or together in the same liquid, semi-solid, or solid delivery form. For example, a microparticulate or nanoparticulate dry solid system could be administered intranasally. Or the combined agents could be both administered transdermally. The two treatments could be incorporated together in a patch, or most preferably in a topical liquid or semi-solid (gel) delivery system. This latter method is most effectively realized in practice for GH agents of the secretagogue (GHSs) variety, such as GHRPs or GHRHs or suitable GHRH fragments that still retain the necessary GH releasing activity. The reason for the suitability is based on the molecular size. It is known throughout the literature that smaller molecules have a higher potential for transdermal delivery than large molecules, such as oligopeptides including GH and IGF-1. The GHrelins and GHRH secretagogues are most preferably selected for the transdermal route based upon small molecular size, such as hexarelin, since transdermal delivery efficiency is good for a hexapeptide. In general, it is preferred that peptides below 30 amino acids are considered for the transdermal delivery format.

Additional clinical studies to confirm the ability of androgen therapy combined with these other hormones to alleviate the symptoms of FMS will be performed. In these studies, the ability of the combined therapy to resolve muscle pain in peri/postmenopausal women diagnosed with FMS will be evaluated. More specifically, patients will be examined for an inverse correlation between serum hormone levels and diminishment in muscle pain. The study will be designed to be similar to the study discussed above in this application. Patients will be assigned randomly to one of the following regimens: 1) placebo twice a day for two months; 2) combination testosterone therapy comprising testosterone and the hormone for testing (e.g., growth hormone) for two months; 3) testosterone for 2 months; or 4) test hormone for two months. These treatments will be followed by a one month washout phase and the patients will again be randomly assigned to one of the above treatment regimens for another two month period.

Patients will be provided with a Patient Questionnaire Form to fill out to assess their symptoms and level of pain in a semi-quantitative manner at the baseline, 2 month and 5 month timepoints. Included in the questionnaire are parameters for patients to evaluate that are common to published and validated FMS patient questionnaires such as sleeplessness, fatigue, headache and stiffness (Wolfe et al., *Arthritis and Rheumatism,* 1990, 33(2):160-172; Goldenberg et al., *Arthritis and Rheumatism,* 1996, 39(11):1852-9; and Burckhardt et al., *J. Rheumatology,* 1991, 18:728-33). The attending physician will also complete a Physician's Form at the baseline, 2 month and 5 month time points to verify that the patient fulfills the criteria for FMS by the American College of Rheumatology, and to document the intensity of the muscle pain for each of the 18 commonly recognized tender points that patients with FMS are known to have.

Patients will be tested at the baseline, 2 month and 5 month time points for total serum hormone levels, serum estradiol levels, cardiac health and liver function. Patients will be tested at a common time of day, preferably a predetermined peak time for the androgen, after fasting since midnight, and on day 3 after the start of their menstrual period if they are still menstruating.

What is claimed is:

1. A pharmaceutical composition formulated for administering a therapeutic female-appropriate amount of an androgen compound to a female human patient who has a condition which is associated with deficient serum androgen levels, said pharmaceutical composition comprising a safe female-appropriate unit dose of said androgen, in a pharmaceutically acceptable carrier formulated for daily topical administration to said female human patient as a gel, the safe female-appropriate unit dose of said androgen being in an amount which is both effective for alleviating the female patient's condition associated with androgen deficiency and for consistently raising the female patients' serum androgen levels only within limits approximating the reference range for normal premenopausal women, wherein the composition contains a daily unit dose of about 7.5 mg of testosterone and is formulated to provide steady state total testosterone serum levels within a range of between about 0.9 ng/mL to about 1.4 ng/mL for at least 24 hours after each daily administration without raising free testosterone serum levels or twenty-four hour free testosterone AUC above the levels required for therapeutic efficacy and safety.

2. The composition according to claim 1 wherein the concentration of androgen is present in an amount of about 1% on a weight basis.

3. The composition according to claim 1 wherein the androgen is selected from the group consisting of testosterone, danazol, fluoxymesterone, oxandrolone, nandrolone decanoate, nandrolone phenpropionate, oxymethalone, stanozolol, methandrostenolone, testolactone, pregnenolone dehydroepiandrosterone, and testosterone derivatives.

4. The composition according to claim 1 wherein the androgen is selected from the group consisting of testosterone, dihydrotestosterone, androstenedione, methyltestosterone, and testosterone esters.

5. The composition according to claim 4 wherein the testosterone ester is selected from the group consisting of testosterone enanthate and testosterone cypionate.

6. A composition according to claim 3 in which the condition which is associated with deficient serum androgen levels is selected from the group consisting of fibromyalgia, chronic fatigue syndrome, and decreased sexual desire and the safe female effective unit dose is an amount which will raise the female human patient's steady state serum androgen level without causing androgenic side effects.

7. The composition of claim 1, wherein the composition formulated to provide steady state total testosterone serum levels within a range of between about 0.9 ng/mL to about 1.4 ng/mL for at least 24 hours after each daily administration without raising free testosterone serum levels above about 4.69 pg/mL or twenty-four hour free testosterone AUC above about 71.38 pg-h/mL.

8. A method of alleviating the symptoms of a condition which is associated with deficient serum androgen levels in a female human patient comprising administering daily to said patient suffering from deficient serum androgen levels a safe and effective amount of the composition of claim 1 which is both effective for alleviating the female patient's condition associated with androgen deficiency and for consistently raising the female patients' serum androgen levels only within limits approximating the reference range for normal premenopausal women, wherein the composition contains a daily unit dose of about 7.5 mg of testosterone and is formulated to provide steady state total testosterone serum levels within a range of between about 0.9 ng/mL to about 1.4 ng/mL for at least 24 hours after each daily administration without raising free testosterone serum levels or twenty-four hour free testosterone AUC above the levels required for therapeutic efficacy and safety.

9. The method of claim 8 wherein the concentration of androgen is present in an amount of about 1% on a weight basis.

10. The method of claim 8 wherein the androgen is selected from the group consisting of testosterone, danazol, fluoxymesterone, oxandrolone, nandrolone decanoate, nandrolone phenpropionate, oxymethalone, stanozolol, methandrostenolone, testolactone, pregnenolone dehydroepiandrosterone, and testosterone derivatives.

11. The method of claim 8 wherein the androgen is selected from the group consisting of testosterone, dihydrotestosterone, androstenedione, methyltestosterone, and testosterone esters.

12. The method of claim 11 wherein the testosterone ester is selected from the group consisting of testosterone enanthate and testosterone cypionate.

13. The method of claim 10 wherein the condition which is associated with deficient serum androgen levels is selected from the group consisting of fibromyalgia, chronic fatigue syndrome, and decreased sexual desire and the safe female effective unit dose is an amount which will raise the female human patient's steady state serum androgen level without causing androgenic side effects.

14. The method of claim 8 wherein the composition is formulated to provide steady state total testosterone serum levels within a range of between about 0.9 ng/mL to about 1.4 ng/mL for at least 24 hours after each daily administration without raising free testosterone serum levels above about 4.69 pg/mL or twenty-four hour free testosterone AUC above about 71.38 pg-h/mL.

* * * * *